United States Patent [19]

Nofre et al.

[11] Patent Number: 4,877,895

[45] Date of Patent: Oct. 31, 1989

[54] GLYCINE AND β ALANINE DERIVATIVES AS SWEETENING AGENTS

[75] Inventors: Claude Nofre, Lyons; Jean M. Tinti, Meyzieu; Farroudja O. Chatzopoulos, Saint Etienne, all of France

[73] Assignee: Universite Claude Bernard - Lyon 1, France

[21] Appl. No.: 836,071

[22] Filed: Mar. 4, 1986

[30] Foreign Application Priority Data

Mar. 19, 1985 [FR] France ................................. 85 04242

[51] Int. Cl.$^4$ ........................................ C07C 121/52
[52] U.S. Cl. .................................... 558/413; 558/414;
558/418; 562/430; 562/434; 562/440; 514/426;
426/548
[58] Field of Search ................ 558/414, 413, 418;
562/430, 434, 440; 564/104

[56] References Cited

U.S. PATENT DOCUMENTS

| | | | |
|---|---|---|---|
| 3,492,131 | 1/1970 | Schlatter | 99/141 |
| 3,642,491 | 2/1972 | Schlatter | 99/28 |
| 3,714,139 | 1/1973 | Schlatter | 260/112.5 |
| 3,800,046 | 3/1974 | Schlatter | 426/168 |
| 4,426,521 | 1/1984 | Tanaka et al. | 544/146 |
| 4,656,678 | 2/1987 | Nofre et al. | 426/548 |
| 4,673,582 | 6/1987 | Nofre et al. | 426/548 |

FOREIGN PATENT DOCUMENTS

| | | |
|---|---|---|
| 1027113 | 2/1978 | Canada . |
| 0048051 | 3/1982 | European Pat. Off. . |
| 2533210 | 9/1982 | France . |

OTHER PUBLICATIONS

Journal of Agricultural and Food Chemistry, vol. 28, No. 6, 1980, pp. 1338–1340.
Chemische Berichte, vol. 94, No. 7, 1961, pp. 1814–1824, Weinheim, DE; F. Micheel et al. with translation.
Joseph W. Tsang et al., Peptide Sweetners, 6, Structural Studies on the C-Terminal Amino Acid of L-Aspartyl Dipeptide Sweetners, American Chemical Society, Jan. 3, 1984, 6 pages.
Y. Ariyoshi et al., The Structure-Taste Relationships of the Dipeptide Esters, Composed of L-Aspartic Acid and B-Hydroxy Amino Acids, Bulletin of the Chemical Society of Japan, 02/1974, pp. 326–330.
Tinti, J. M. et al., Studies on Sweetners Requiring the Simultaneous Presence of Both the $NO_2/CN$ and COO-Groups, Naturwissenschaften 68, Dec. 1981, pp. 143–145.
Tinti, J. M. et al., Sweet Taste Receptor, Naturwissenschaften 67, Jan. 2, 1980, pp. 193–194.
Miller, et al., A Facile Conversion of Amino Acids to Guanidinio Acids, Communications, Sep. 1986, pp. 777–779.

Primary Examiner—Anton H. Sutto
Attorney, Agent, or Firm—Arnold, White & Durkee

[57] ABSTRACT

Sweetening agents, characterized in that they conform to the following formula:

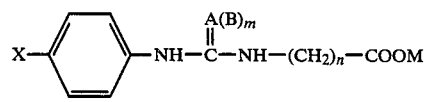

wherein:

A is an imino (=N—), iminium (=N$^+$<), methylene (=C<) group, the iminium group being able to be salified by a physiologically acceptable anion;

m and n are number equal to 1 or 2;

B:
when n=1, represents H, CN, $OCH_3$, $NO_2$, $SO_2R$, SOR, $SO_2NHR$, $SO_2NR_2$, wherein R is an alkyl, cycloalkyl or aryl group having up to 10 carbon atoms;
when n=2, represents H, CN, $OCH_3$;

X:
represents CN, $NO_2$, when B is H, CN, $OCH_3$;
represents CN, $NO_2$, $COCH_3$, CHO, Cl, $CF_3$, F, H, when B is $NO_2$, $SO_2R$, SOR, $SO_2NHR$, $SO_2NR_2$;

M is a hydrogen atom or a physiologically acceptable organic or inorganic cation.

7 Claims, No Drawings

GLYCINE AND β ALANINE DERIVATIVES AS SWEETENING AGENTS

The present invention relates to new sweetening agents used for sweetening food, drinks, confectionary, chewing gums, hygiene products, cosmetics, pharmaceutical and veterinary products, etc. . . It also relates to the products and compositions containing such sweetening agents.

Among the chemical compounds presenting sweetening properties, "suosan" and its derivatives constitute a chemical series which has been widely studies since their discovery in 1948 by Petersen and Muller (cf. for example Beets, Structure-Activity Relationships in Human Chemoreception, Applied Science Publ., London, 1978, pp. 336–337; Crosby and Wingard, in Developments in Sweeteners, Applied Science Publ., London, 1979, p. 160; Tinti, Nofre and Peytavi, Z. Lebensm. Unters. Forsch., 1982, 175, 266–268). However, these compounds have never been used in practice as certain of them release potentially toxic molecules; this is the case of "suosan" which leads to p-nitroaniline. Finally, certain of these compounds present, apart from their sweet taste, an undesirable liquorice or bitter aftertaste.

It is an object of the present invention to overcome these drawbacks.

It relates to sweetening agents which are characterized in that they conform to the formula:

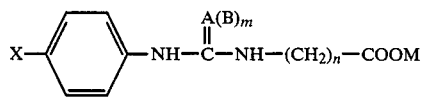

wherein:
A is an imino (=N—), iminium (=N+ <), methylene (=C<) group, the iminium group being able to be salified by a physiologically acceptable organic or inorganic anion;
m and n are numbers equal to 1 or 2;
B:
when n=1, represents H, CN, OCH$_3$, NO$_2$, SO$_2$R, SOR, SO$_2$NHR, SO$_2$NR$_2$, wherein R is an alkyl, cycloalkyl or aryl group having up to 10 carbon atoms, 1 or 2 carbon atoms being able to be substituted by 1 or 2 sulfur or oxygen atoms;
when n=2, represents H, CN, OCH$_3$;
X:
represents CN, NO$_2$, when B is H, CN, OCH$_3$;
represents CN, NO$_2$, COCH$_3$, CHO, Cl, CF$_3$, F, H, when B is NO$_2$, SO$_2$R, SOR, SO$_2$NHR, SO$_2$NR$_2$;
M is a hydrogen atom or a physiologically acceptable organic or inorganic cation.

"Physiologically acceptable" anion or cation is understood to mean any anion or cation which does not present any appreciable toxicity for the organism.

In a preferred embodiment:
A is an imino (=N—), iminium (=N+ <), methylene (=C<) group, the iminium group being able to be salified by a chloride ion;
B:
when n=1, represents H, CN, OCH$_3$, NO$_2$, SO$_2$R, wherein R is a normal or branched alkyl group having up to 5 carbon atoms, isohexyl, phenyl (C$_6$H$_5$), cyclohexyl (C$_6$H$_{11}$), benzyl (C$_6$H$_5$CH$_2$), tolyl (CH$_3$C$_6$H$_4$), cyclohexylmethyl (C$_6$H$_{11}$CH$_2$);
when n=2, represents H, CN, OCH$_3$;
X is CN;
M is a hydrogen atom or a cation selected from the group Na$^+$, K$^+$, NH$_4^+$, ½ Ca$^{2+}$, 1/2 Mg$^{2+}$.
Advantageously, in practice:
The sweetening agent is characterized in that it comprises a compound of formula:

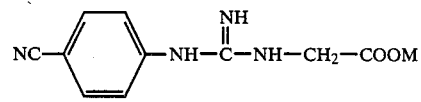

The sweetening agent is characterized in that it comprises a compound of formula:

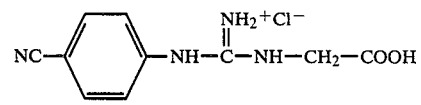

The sweetening agent is characterized in that it comprises a compound of formula:

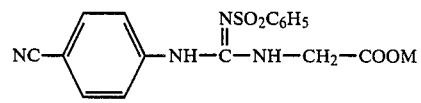

The sweetening agent is characterized in that it comprises a compound of formula:

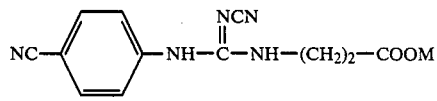

In other words, the invention relates to improved derivatives of "suosan" which are characterized in particular by the replacement of the ureido or thioureido groups by guanidino, guanidinium or 1,1-diaminoethenyl groups, these groups being able to be substituted by the groups CH, OCH$_3$, NO$_2$, SO$_2$R, SOR, SO$_3$NHR, SO$_2$NR$_2$.

This improvement unexpectedly presents the advantage not only of conserving a sweet taste for these new compounds, but also of enhancing very often the sweetening power with respect to that of the ureido or thioureido derivatives, since compounds are obtained by this improvement which are up to 45000 (forty five thousand) times sweeter than sucrose. In Chemical Abstracts (vol. 82, 1975, n° 140061p) Y. Yuki and K. Inoue (Nippon Kagaku Kaishi, 1974, no. 11, 2140-3) described the N-[(4-chlorophenylamino)iminomethyl]-β-alanine (Chemical Substance Index, vol. 76-85, 1972–1976, p. 1067cs); this chloro derivative, contrary to the compounds of the invention, does not present sweetness properties, which proves the unforeseeable nature of the invention.

The improvement also makes it possible to eliminate the bitter or liquorice aftertaste which the corresponding ureido or thioureido derivatives often present. In fact, it is not possible to differentiate the new compounds thus obtained from sucrose simply by the organoleptic properties.

The invention also relates to the process which comprises sweetening a product by adding thereto such a sweetening agent in an effective amount; it also relates to the product thus sweetened. "Effective amount" means the quantity which could be detected by the physiologic senses of human. Finally, it relates to any composition including such a sweetening agent associated with a compatible carrier or with another sweetening agent.

The compounds according to the invention may be prepared by condensation between compounds of the following formulas:

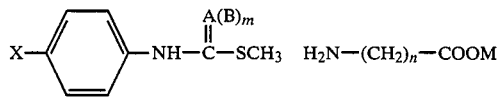

The reaction between these two compounds may be carried out in the presence of a base, the base being chosen in the group comprising sodium hydroxide, potassium hydroxide or a tertiary amine like, for instance, triethylamine. The condensation is carried out at boiling point in an ethanol-water mixture.

The sweetening potency of the compounds was assessed by a panel of six trained tasters. To this end, the compounds, in aqueous solution at variable concentrations, are compared, from the standpoint of taste, with control solutions of sucrose at concentrations of 2%, 5%, and 10%, respectively, i.e. at concentrations corresponding to those used currently; in fact, the sweetening potency of the synthetic sweeteners varies depending on the concentration of the solution of sucrose used as reference. The sweetening potency of the compound tested with respect to sucrose then corresponds to the ratio by weight which exists between the compound and the sucrose at equal sweetening potency, i.e. when the sweet tastes between the solution of the compound tested and the control solution of sucrose are considered, by a majority of tasters, to have the same sweetening potency.

The manner in which the invention may be carried out and the advantages following therefrom will be more readily seen from the following examples given by way of indicative and non-limiting examples.

EXAMPLE 1

Synthesis of N-[cyanoimino(4-cyanophenylamino)methyl]-3-aminopropanoic acid:

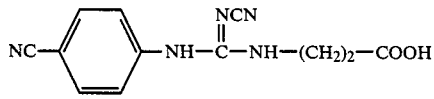

A mixture of 32 g (0.1 mol) of 4-cyanophenyl isothiocyanate and of 12.8 g (0.2 mol) of monosodium cyanamide in 100 cm³ of absolute ethanol is maintained for 2 hours at boiling point. After cooling, the precipitate obtained is filtered and washed with 200 cm³ of absolute ethanol. The solid is then placed in suspension in a solution of dimethyl sulfate (25 g, 0.2 mol) in 500 cm³ of ethanol; the mixture is heated for two hours at boiling point. The final precipitate is filtered, washed with 2×100 cm³ of water and with 2×100 cm³ of ethanol, then is dried in vacuo. 32.8 g (yield 70%) of N-(4-cyanophenyl)-N'-cyano-S-methylisothiourea are obtained:

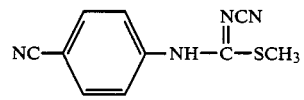

which is a white solid, whose melting point is 225°–230° C.

A mixture of 12.3 g (0.138 mol) of β-alanine and of 5.52 g (0.138 mol) of sodium hydroxide in 100 cm³ of water is added to a solution of 20 g (0.092 mol) of N-(4-cyanophenyl)-N'-cyano-S-methylisothiourea in 300 cm³ of 95% ethanol. The mixture is heated to reflux for 4 hours. After cooling, the solution is filtered then concentrated to dryness in vacuo. The residue obtained is dissolved in 200 cm³ of a 2% sodium carbonate solution. The resulting solution is washed by dichloromethane (3×50 cm³) then acidified by a 3N HCl solution until a pH close to 2 is obtained. The white solid formed is filtered, then washed with water (2×10 cm³) and dried in vacuo. After recrystallization in water, 15 g (yield 63%) of N-[cyanoimino(4-cyanophenylamino)methyl]-3-aminopropanoic acid, which is a solid having a melting point of 158°–162° C., are obtained.

The salts of sodium, potassium and calcium of this acid were obtained by dissolution of 1 g of acid in 10 cm³ of water containing 0.15 g of NaOH, 0.21 g of KOH, 0.14 g of Ca(OH)₂, respectively. After concentration to dryness and recrystallization in water, the salts obtained have a melting point of 261° C. for the sodium salt, 260° C. for the potassium salt, 236° C. for the calcium salt.

These compounds, both the acid and the salts, all have an intense sweet taste, quite comparable to that of sucrose, without any aftertaste. Their sweetening potency corresponds approximately, on a weight basis, to 900 (nine hundred) times that of sucrose comparatively to a 2% sucrose solution, to 500 (five hundred) times with respect to a 5% sucrose solution, to 400 (four hundred) times with respect to a 10% sucrose solution.

EXAMPLE 2

Synthesis of N-[cyanoimino(4-cyanophenylamino)methyl]-2-aminoethanoic acid:

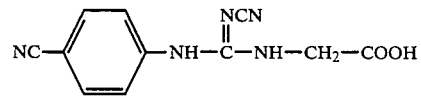

This compound is obtained from glycine and N-(4-cyanophenyl)-N'-cyano-S-methylisothiourea, following the experimental procedure described in example 1 (yield 70%; melting point 103°–105 ° C., acetone-dichloromethane). Its sodium salt has a melting point of 178° C. (H₂O), its calcium salt, 184° C. (H₂O).

These compounds have an intense sweet taste. Their sweetening potency corresponds approximately, on a weight basis, to 7000 (seven thousand) times that of sucrose with respect to a 2% sucrose solution, to 5000 (five thousand) times with respect to a 5% sucrose solution, to 2000 (two thousand) times with respect to a 10% sucrose solution.

EXAMPLE 3

Synthesis of N-[cyanoimino)4-nitrophenylamino)methyl]-3-aminopropanoic acid:

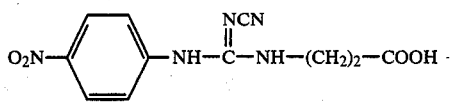

This compound is obtained from β-alanine and N-(4-nitrophenyl)-N'-cyano-S-methylisothiourea, following the experimental procedure described in Example 1 (yield 64%; melting point 165° C. from water).

The sweetening potency of this compound corresponds approximately, on a weight basis, to 900 (nine hundred) times that of sucrose with respect to a 2% sucrose solution, to 500 (five hundred) times with respect to a 5% sucrose solution, to 400 (four hundred) times with respect to a 10% sucrose solution.

EXAMPLE 4

Synthesis of N-[2,2-dicyano(4-cyanophenylamino)ethenyl]-3-aminopropanoic acid:

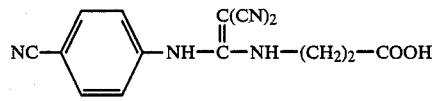

2.88 g of sodium hydride (in 50% dispersion in liquid paraffin), are added, in several fractions, to a solution, cooled to 0° C., of 3.96 g (0.06 mol) of malononitrile dissolved in 30 cm$^3$ of dimethylformamide. The solution is then maintained for 10 minutes at 10° C. before the addition of 9.6 g (0.06 mol) of 4-cyanophenyl isothiocyanate dissolved in 20 cm$^3$ of dimethylformamide. The reaction mixture is maintained for 15 minutes at 20° C. then concentrated to dryness in vacuo. The residue obtained is triturated in boiling chloroform (5×50 cm$^3$) and the final solid obtained is dried in vacuo. 14 g of the solid thus obtained is then placed in contact for 2 hours at 20° C. with 7.8 g of dimethyl sulfate dissolved in 200 cm$^3$ of 95% ethanol. After elimination of ethanol and washing of the remaining solid by water (4×50 cm$^3$), 9,4 g (yield 70%) of 1,1-dicyano-2-(4-cyanophenylamino)-2-(methylthio)-ethene (melting point 160° C.) are obtained after drying:

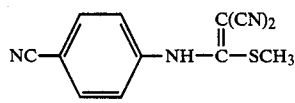

Thereafter are mixed 12.5 g (0.14 mol) of β-alanine, 24 g (0.1 mol) of the compound obtained previously and 5.6 g (0.14 mol) of sodium hydroxide in a solution of 200 cm$^3$ of ethanol heated to boiling point. The reaction mixture is concentrated to dryness after 4 hours of contact and the residue obtained is dissolved in 200 cm$^3$ of a 2% aqueous sodium carbonate solution. The solution is washed with dichloromethane (3×50 cm$^3$) then acidified by a 3N HCl solution. The precipitate obtained is filtered then washed with water (2×10 cm$^3$). 15 g (yield 55%) of N-[2,2-dicyano(4-cyanophenylamino)ethenyl]-3-aminopropanoic acid, which is a white solid whose melting point is 201° C. (acetone-hexane), are obtained.

The sweetening potency of this compound corresponds approximately, on a weight basis, to 500 (five hundred) times that of sucrose with respect to a 2% sucrose solution, to 120 (one hundred and twenty) times with respect to a 5% sucrose solution, to 60 (sixty) times with respect to a 10% sucrose solution.

EXAMPLE 5

Synthesis of N-[2,2-dicyano(4-cyanophenylamino)ethenyl]-2-aminoethanoic acid:

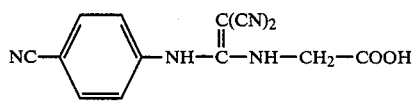

This compound is obtained from glycine and 1,1-dicyano-2-(4-cyanophenylamino)-2-(methylthio)-ethene, following the experimental procedure described in Example 4 (yield 50%; melting point 100° C., acetone-dichloromethane).

The sweetening potency of this compound corresponds approximately, on a weight basis, to 4000 (four thousand) times that of sucrose with respect to a 2% sucrose solution, to 2500 (two thousand five hundred) time with respect to a 5% sucrose solution, to 1300 (one thousand three hundred) times with respect to a 10% sucrose solution.

EXAMPLE 6

Synthesis of N-[4-cyanophenylamino(imino)methyl]-3-aminopropanoic acid:

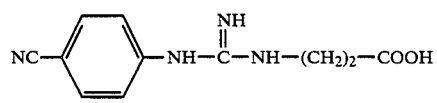

To a solution of 6.7 g (0.037 mol) of 4-cyanophenylthiourea in 150 cm$^3$ of 2-butanone, 13.1 g (0.092 mol) of methyl iodide are added. After 24 hours of contact at room temperature, the solid formed is filtered, washed with 2-butanone (2×20 cm$^3$) then with ethyl ether (2×50 cm$^3$), which makes it possible to obtain 9.2 g (yield 76%; melting point 212° C.) of N-(4-cyanophenyl)-S-methylisothiourea hydroiodide:

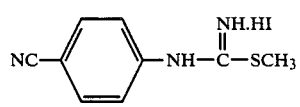

A mixture of 4.18 g (47 mmol) of β-alanine, of 1,88 g (47 mmol) of sodium hydroxide in 20 cm$^3$ of water and of 15 g (47 mmol) of N-(4-cyanophenyl)-S-methylisothiourea hydroiodide in 100 cm$^3$ of 95% ethanol is heated to reflux for 5 hours. The precipitate formed is filtered, then dissolved in 150 cm$^3$ of 1N aqueous sodium hydroxide solution. The solution obtained is washed with ethyl acetate (3×50 cm$^3$), then neutralized to pH 7 by a concentrated HCl solution. The precipitate obtained is filtered, washed with hot absolute ethanol, then recrystallized in water. 7 g (yield 65%) of N-[4-cyanophenylamino(imino)methyl]-3-aminopropanoic acid, having a melting point of 233°–235° C., are obtained.

The sweetening potency of this compound corresponds approximately, on a weight basis, to 300 (three hundred times that of sucrose with respect to a 2% sucrose solution, to 180 (one hundred and eighty) times with respect to a 5% sucrose solution.

EXAMPLE 7

Synthesis of N-[4-cyanophenylamino(imino)methyl]-2-aminoethanoic acid:

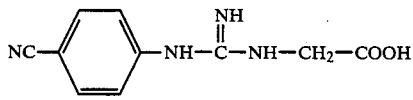

This compound is obtained from glycine and N-(4-cyanophenyl)-S-methylisothiourea hydroiodide, following the experimental procedure described in Example 6 (yield 53%; melting point 275° C., H₂O).

The hydrochloride of this compound:

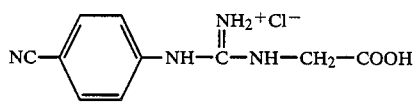

is obtained by concentration to dryness of a solution of 1 g of N-[4-cyanophenylamino(imino)methyl]-2-aminoethanoic acid in 15 cm³ of a 1N HCl solution. Its melting point is 197° C.

The sodium salt of N-[4-cyanophenylamino(imino)methyl]-2-aminoethanoic acid is obtained after dissolution of 1 g of N-[4-cyanophenylamino(imino)methyl]-2-aminoethanoic acid in 4.58 cm³ of a 1N sodium hydroxide solution followed by a concentration to dryness. The residue obtained is solubilized in acetone. The solution is filtered, then concentrated to dryness, which makes it possible to obtain 1.1 g of the corresponding sodium salt (melting point 232° C.).

The sweetening potency of N-[4-cyanophenylamino(imino)methyl]-2-aminoethanoic acid or of its salts (hydrochloride or sodium salt) corresponds approximately, on a weight basis, to 2700 (two thousand seven hundred) times that of sucrose with respect to a 2% sucrose solution, to 1600 (one thousand six hundred) times with respect to a 5% sucrose solution, to 600 (six hundred) times with respect to a 10% sucrose solution.

EXAMPLE 8

Synthesis of N-[methoxyimino(4-cyanophenylamino) methyl]-3-aminopropanoic acid:

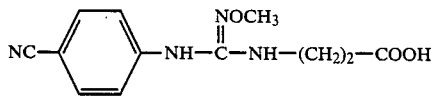

This compound is obtained from β-alanine and N-(4-cyanophenyl-N'-methoxy-S-methylisothiourea, following the experimental procedure described in Example 1 (yield 10%, melting point 155° C.).

The sweetening potency of this compound corresponds approximately, on a weight basis, to 300 (three hundred) times that of sucrose with respect to a 2% sucrose solution, to 100 (one hundred) times with respect to a 5% sucrose solution, to 50 (fifty) times with respect to a 10% sucrose solution.

EXAMPLE 9

Synthesis of N-[2-nitro(4-cyanophenylaminoethenyl]2-aminoethanoic acid:

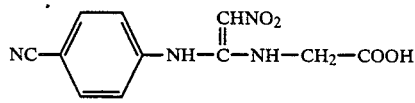

A mixture of 8.3 g (0.05 mol) of 1-nitro-2,2-(methylthio)-ethene and of 8.85 g (0.075 mol) of 4-aminobenzonitrile in 40 cm³ of glacial acetic acid is heated at boiling point for 2 hours. After cooling the precipitate obtained is filtered, washed with glacial acetic acid (5 cm³), ethanol (2×10 cm³), acetone (2×10 cm³) and ethyl ether (2×10 cm³). The resulting solid is recrystallized in dimethylsulfoxide. 3 g (yield 30%) of 1-nitro-2-(4-cyanophenylamino-2-(methylthio)-ethene having a melting point of 188°–190 ° C. are obtained:

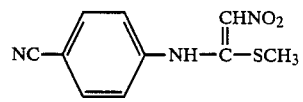

A mixture containing 0.15 g (2 mmol) of glycine, 0.41 g (2 mmol) of 1-nitro-2-(4-cyanophenylamino)2-(methylthio)-ethene and 0.27 cm³ (2 mmol) of triethylamine in 20 cm³ of ethanol-water (5-1) is heated at boiling point for 3 hours. After concentration in vacuo the residue obtained is dissolved in 20 cm³ of 1N sodium hydroxide and the solution obtained is washed with ethyl acetate (4×10 cm³) then acidified to a pH close to 3 with a 6N HCl solution. The white solid obtained is filtered, washed with water (2×2 cm³) and dried in vacuo. 0.2 g (yield 38%) of N-[2-nitro(4-cyanophenylamino)ethyl]-2-aminoethanoic acid having a melting point of 230° C. is obtained.

The sweetening potency of this compound corresponds approximately, on a weight basis, to 9000 (nine thousand) times that of sucrose with respect to a 2% sucrose solution, to 6000 (six thousand) times with respect to a 5% sucrose solution, to 2700 (two thousand seven hundred) times with respect to a 10% sucrose solution.

EXAMPLE 10

Synthesis of N-[phenylsulfonylimino(4-cyanophenylamino-methyl]-2-aminoethanoic acid:

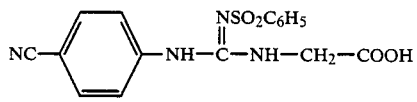

A mixture of 5 g (0.031 mol) of 4-cyanophenyl isothiocyanate, of 6.3 g (0.04 mol) of benzenesulfonamide in 50 cm³ of acetone and of 1.6 g (0.04 mol) of sodium hydroxide in 3 cm³ of water is maintained for two hours at room temperature. The precipitate obtained is filtered, washed with acetone and ethyl ether (2×20 cm³). The final solid (9 g; yield 94%) is then placed in 50 cm³ of 95% ethanol containing 2.75 cm³(0.044 mol) of methyl iodide. After 24 hours at room temperature the solution is concentrated to dryness and the residue is washed with ethyl ether (3×20 cm³) and dried in vacuo. 8.5 g (yield 80%) of N-(4-cyanophenyl)-N'-phenylsulfonyl-S-methylisothiourea (melting point 150° C.) is obtained:

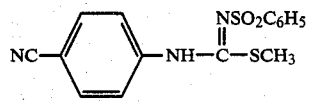

A mixture of 0.57 g (7.6 mmol) of glycine, of 0.3 g (7.6 mmol) of sodium hydroxide in 3 cm³ of water and of 2.5 g (7.6 mmol) of N-(4-cyanophenyl)-N'-phenylsulfonyl-S-methylisothiourea in 30 cm³ of 95% ethanol is heated at boiling point for 7 hours. After cooling the precipitate obtained is filtered and dissolved in 20 cm³ of a 1N solution hydroxide solution. The solution obtained is washed with dichloromethane (3×10 cm³) and ethyl acetate (2×10 cm³) then acidified to a pH close to 3 with a 6N HCl solution. After cooling, the precipitate obtained is filtered, washed with water (2×5 cm³) and dried in vacuo to give 1.4 g (yield 52%) of N-[phenyl-sulfonylimino(4-cyanophenylamino-methyl]-2-amino ethanoic acid having a melting point of 133° C.

The sweetening potency of this compound corresponds approximately, on a weight basis, to 45,000 (forty five thousand) times that of sucrose with respect to a 2% sucrose solution, to 25,000 (twenty five thousand) times with respect to a 5% sucrose solution, to 15000 (fifteen thousand) times with respect to a 10% sucrose solution.

EXAMPLE 11

Synthesis of N-[phenylsulfonylimino(4-acetyl-phenylamino-methyl]-2-aminoethanoic acid:

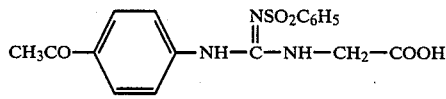

This compound is obtained from glycine and N-(4-acetylphenyl)-N'-phenylsulfonyl-S-methylisothiourea following the experimental procedure described in Example 10 (yield 38%, melting point 171° C.).

The sweetening potency of this compound corresponds approximately, on a weight basis, to 850 (height hundred and fifty) times that of sucrose with respect to a 2% sucrose solution, to 750 (seven hundred and fifty) times with respect to a 5% sucrose solution, to 550 (five hundred and fifty) times with respect to a 10% sucrose solution.

EXAMPLE 12

Synthesis of N-[phenylsulfonylimino(4-chloro-phenylamino-methyl]-2-aminoethanoic acid:

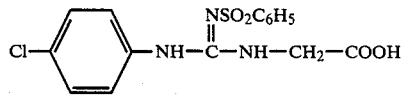

This compound is obtained from glycine and N-(4-chlorophenyl)-N'-phenylsulfonyl-S-methylisothiourea, following the experimental procedure described in Example 10 (yield 30%; melting point 133° C.).

The sweetening potency of this compound corresponds approximately, on a weight basis, to 2000 (two thousand) times that of sucrose with respect to a 2% sucrose solution, to 1400 (one thousand and four hundred) times with respect to a 5% sucrose solution, to 750 (seven hundred and fifty) times with respect to a 10% sucrose solution.

EXAMPLE 13

Synthesis of N-[methylsulfonylimino(4-cyanophenylamino)methyl]-2-aminoethanoic acid:

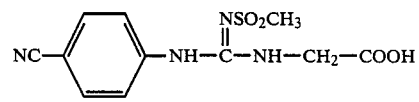

This compound is obtained from glycine and N-(4-cyanophenyl)-N'-methylsulfonyl-S-methylisothiourea, following the experimental procedure described in Example 10 (yield 55%; melting point 170° C.).

The sweetening potency of this compound corresponds approximately, on a weight basis, to 4000 (four thousand) times that of sucrose with respect to a 2% sucrose solution, to 2500 (two thousand and five hundred) times with respect to a 5% sucrose solution, to 1400 (one thousand and four hundred) times with respect to a 10% sucrose solution.

EXAMPLE 14

Synthesis of N-[phenylsulfonylimino(phenylamino) methyl]-2-aminoethanoic acid:

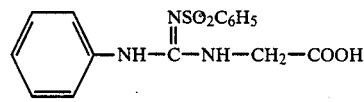

This compound is obtained from glycine and N-phenyl-N'-phenylsulfonyl-S-methylisothiourea, following the experimental procedure described in Example 10 (yield 10%; melting point 148° C.).

The sweetening potency of this compound corresponds approximately, on a weight basis, to 900 (nine hundred) times that of sucrose with respect to a 2% sucrose solution, to 800 (height hundred) times with respect to a 5% sucrose solution, to 600 (six hundred) times with respect to a 10% sucrose solution.

Taking into account the advantages already mentioned for these sweetening agents, namely:

high sweetening potency, no bitter or liquorice aftertaste, stability in solution, and taking into account the fact that these compounds are non-nutritive, non-fermentable and non-cariogenic, these compounds may be successfully used, alone or in association with other sweetening agents, to sweeten numerous products, such as for instance, by way of non-limiting examples:

as tabletop nonnutritive sweeteners (in the form of tablets, packets, etc. . . ), in low-calorie and dietetic foods, such as for example in carbonated beverages (cola, lemonade and fruit drinks, beer, etc. . . ) or still beverages (fruit or vegetable juices, syrups, coffee, tea, chocolate, etc. . . ) and drink concentrates or powdered instant drinks, in presweetened instant coffee, tea, chocolate drinks, in dairy product (milk and yoghurts), presweetened powdered milk, whipped cream, etc. . . ) or similar dairy products, in presweetened breakfast cereals and drinks, in desserts (gelatin-based desserts, cooked or instant puddings and other cakes and pastries) and in deep-frozen desserts, ice creams and whipped toppings, in bakery products, in dietetic jams, marmalades, jellies, preserves and honeys, in dressing, ketchups, pickles, sauces and other food flavorings, in confectionery (candies, chewy candies, chocolate or cocoa confectionery, marshmallows, gums and other confectionery products), in chewing gums, in dentifrices and lipsticks, in mouthwashes and gargles, in various pharmaceutical, veterinary and cosmetic preparations (to improve the taste of the preparation or to cover the unpleasant taste of certain products), in various hygiene articles, in tobaccos, in animal foods, etc. . .

The sweetening agents of this invention may be advantageously used in mixture with a carrier therefor, like for instance, by a non-limiting way, starch and malto-dextrins, cellulose, methylcellulose, carboxymethylcellulose, sodium alginate, pectins, gums, lactose, maltose, glucose, leucine, glycerol, mannitol, sorbitol, phosphoric, citric, tartaric, fumaric, benzoic, sorbic, propanoic acids, their sodium, potassium and calcium salts, sodium bicarbonate.

The sweetening agents of this invention may be used in association with other sweetening agents like for instance, by a non-limiting way, sucrose, corn syrups, fructose, aspartame, clycyrrhizin, xylitol, acesulfame-K, thaumatin.

We claim:

1. Sweetening agents, characterized in that they respond to the following general formula:

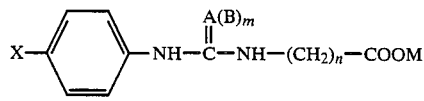

wherein:

A is an imino (=N—), iminium (=N<), methylene (=C,) group, the iminium group being able to be salified by a chloride ion;

m is a number equal to 1 when A is an imino group and is equal to 2 when A is a methylene or iminium group;

n is a number equal to 1 or 2;

B:

when n=1, represents H, CN, OCH3, NO2, SO2R, wherein R is an alkyl, cycloalkyl or aryl group having up to 10 carbon atoms, or such a group wherein 1 or 2 carbon atoms are substituted by 1 or 2 sulfur or oxygen atoms;

when n=2, represents H, CN, OCH3;

X:

represents CN, NO2, when B is H, CN, or OCH3;

represents CN, NO2, COCH3, Cl, F, H, when B is NO2, or SO2R;

M is a hydrogen atom or a physiologically acceptable organic or inorganic cation.

2. Sweetening agents according to claim 1 characterized in that:

B:

when n=1, represents SO2CH3 or SO2C6H5;

when n=2, represents H, CN;

X is CN;

and M is a hydrogen atom or a cation selected from the group comprising Na+, K+, NH4, Ca2+, ½ Mg2+.

3. Sweetening agents according to claim 2 characterized in that is comprises a compound of formula:

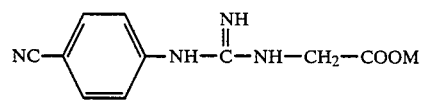

4. Sweetening agents according to claim 2 characterized in that is comprises a compound of formula:

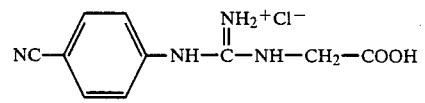

5. Sweetening agents according to claim 2 characterized in that is comprises a compound of formula:

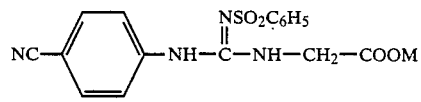

6. Sweetening agents according to claim 2 characterized in that it comprises a compound of formula:

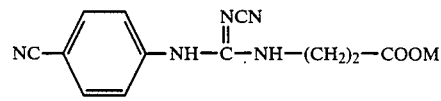

7. Sweetening compositions characterized in that they comprise an effective amount of a sweetening agent according to claim 1 and a carrier therefor, the carrier being chosen in the group comprising starch and malto-dextrins, cellulose, methylcellulose and carboxymethylcellulose, sodium alginate, pectins, gums, lactose, maltose and glucose, leucine, glycerol, mannitol and sorbitol, phosphoric acids and their sodium, potassium and calcium salts, sodium bicarbonate.

* * * * *